(12) United States Patent
Ross et al.

(10) Patent No.: US 10,080,586 B2
(45) Date of Patent: *Sep. 25, 2018

(54) DYNAMIZATION MODULE FOR EXTERNAL FIXATION STRUT

(71) Applicant: TEXAS SCOTTISH RITE HOSPITAL FOR CHILDREN, Dallas, TX (US)

(72) Inventors: John David Ross, Ovilla, TX (US); Mikhail L. Samchukov, Coppell, TX (US); Alexander M. Cherkashin, Flower Mound, TX (US); John G. Birch, Dallas, TX (US)

(73) Assignee: Texas Scottish Rite Hospital For Children, Dallas, TX (US)

( * ) Notice: Subject to any disclaimer, the term of this patent is extended or adjusted under 35 U.S.C. 154(b) by 134 days.

This patent is subject to a terminal disclaimer.

(21) Appl. No.: 15/076,209

(22) Filed: Mar. 21, 2016

(65) Prior Publication Data

US 2016/0310168 A1   Oct. 27, 2016

Related U.S. Application Data

(63) Continuation of application No. 14/260,134, filed on Apr. 23, 2014, now Pat. No. 9,289,238.

(51) Int. Cl.
*A61B 17/66* (2006.01)
*A61B 17/60* (2006.01)
(Continued)

(52) U.S. Cl.
CPC .............. *A61B 17/66* (2013.01); *A61B 17/60* (2013.01); *A61B 17/62* (2013.01); *A61B 17/64* (2013.01);
(Continued)

(58) Field of Classification Search
CPC .................... A61B 17/60; A61B 17/62; A61B 17/64–17/666; A61B 17/66; A61B 17/6491; A61B 17/6458
See application file for complete search history.

(56) References Cited

U.S. PATENT DOCUMENTS

| 5,207,676 A | 5/1993 | Canadell et al. |
| 5,275,599 A | 1/1994 | Zbikowski et al. |

(Continued)

FOREIGN PATENT DOCUMENTS

| EP | 2085037 A1 | 5/2009 |
| WO | 2009/018349 A2 | 2/2009 |
| WO | 2009/102904 A1 | 8/2009 |

OTHER PUBLICATIONS

Kristiansen, Leif Pal, Thesis: Biomechanics Laboratory, Department of Orthopaedics, Rikshospitalet, University of Oslo, Norway, "Reconstructive surgery of the human tibia by use of external ring fixator and the Ilizarov method," (2009), Acta Orthopaedica Supplementum, No. 331, vol. 80, 48 pages.

(Continued)

Primary Examiner — Jacqueline Johanas
(74) Attorney, Agent, or Firm — Baker & McKenzie LLP

(57) ABSTRACT

The present disclosure relates to an external fixation apparatus comprising a strut having a longitudinal axis defined therein, the strut comprising a strut housing having a housing adjustment aperture, an adjustment sleeve slidably disposed within the strut housing, and a fastener that releasably couples the strut housing with the adjustment sleeve. An embodiment of the adjustment sleeve comprises a first and a second bore extending from a top towards a bottom surface of the adjustment sleeve, a first sleeve member with a proximal end, a distal end, and an axial bore, and a second sleeve member adjoining the first sleeve member. In an embodiment, the second sleeve member comprises a body (Continued)

and a beveled end that is slidably disposed within the axial bore of the first sleeve member. The adjustment sleeve further comprises a biasing mechanism between the first sleeve member and the second sleeve member.

27 Claims, 13 Drawing Sheets

(51) Int. Cl.
*A61B 17/62* (2006.01)
*A61B 17/64* (2006.01)

(52) U.S. Cl.
CPC .... *A61B 17/6491* (2013.01); *A61B 2017/606* (2013.01)

(56) References Cited

U.S. PATENT DOCUMENTS

| | | | |
|---|---|---|---|
| 5,314,426 A | 5/1994 | Pohl et al. |
| 5,429,638 A | 7/1995 | Muschler et al. |
| 5,451,225 A | 9/1995 | Ross, Jr. et al. |
| 5,626,579 A | 5/1997 | Muschler et al. |
| 5,863,292 A | 1/1999 | Tosic |
| 5,871,484 A | 2/1999 | Spievack et al. |
| 5,928,230 A | 7/1999 | Tosic |
| 5,935,127 A | 8/1999 | Border |
| 7,632,271 B2 | 12/2009 | Baumgartner et al. |
| 8,057,474 B2 | 11/2011 | Knuchel et al. |
| 8,162,984 B2 | 4/2012 | Weirich et al. |
| 8,172,885 B2 | 5/2012 | Songer et al. |
| 8,197,490 B2 | 6/2012 | Pool et al. |
| 8,221,467 B2 | 7/2012 | Butler et al. |
| 8,444,644 B2 | 5/2013 | Ross et al. |
| 8,506,566 B2 | 8/2013 | Karidis et al. |
| 8,574,232 B1 | 11/2013 | Ross et al. |
| 9,078,700 B2 | 7/2015 | Ross et al. |
| 2002/0165500 A1 | 11/2002 | Bechtold et al. |
| 2005/0143735 A1 | 6/2005 | Kyle |
| 2006/0129247 A1 | 6/2006 | Brown et al. |
| 2006/0177264 A1 | 8/2006 | Baumgartner et al. |
| 2007/0118122 A1 | 5/2007 | Butler et al. |
| 2007/0173837 A1 | 7/2007 | Chan et al. |
| 2009/0198236 A1 | 8/2009 | Steiner et al. |
| 2012/0123414 A1 | 5/2012 | Steiner et al. |
| 2012/0136356 A1 | 5/2012 | Doherty et al. |
| 2012/0209269 A1 | 8/2012 | Pool et al. |
| 2012/0303028 A1 | 11/2012 | Wong |
| 2013/0023876 A1 | 1/2013 | Rabiner et al. |
| 2013/0253513 A1 | 9/2013 | Ross et al. |
| 2014/0135764 A1 | 5/2014 | Ross et al. |

OTHER PUBLICATIONS

International Search Report and Written Opinion, PCT/US2015/028719, dated Jun. 30, 2015, 12 pages.

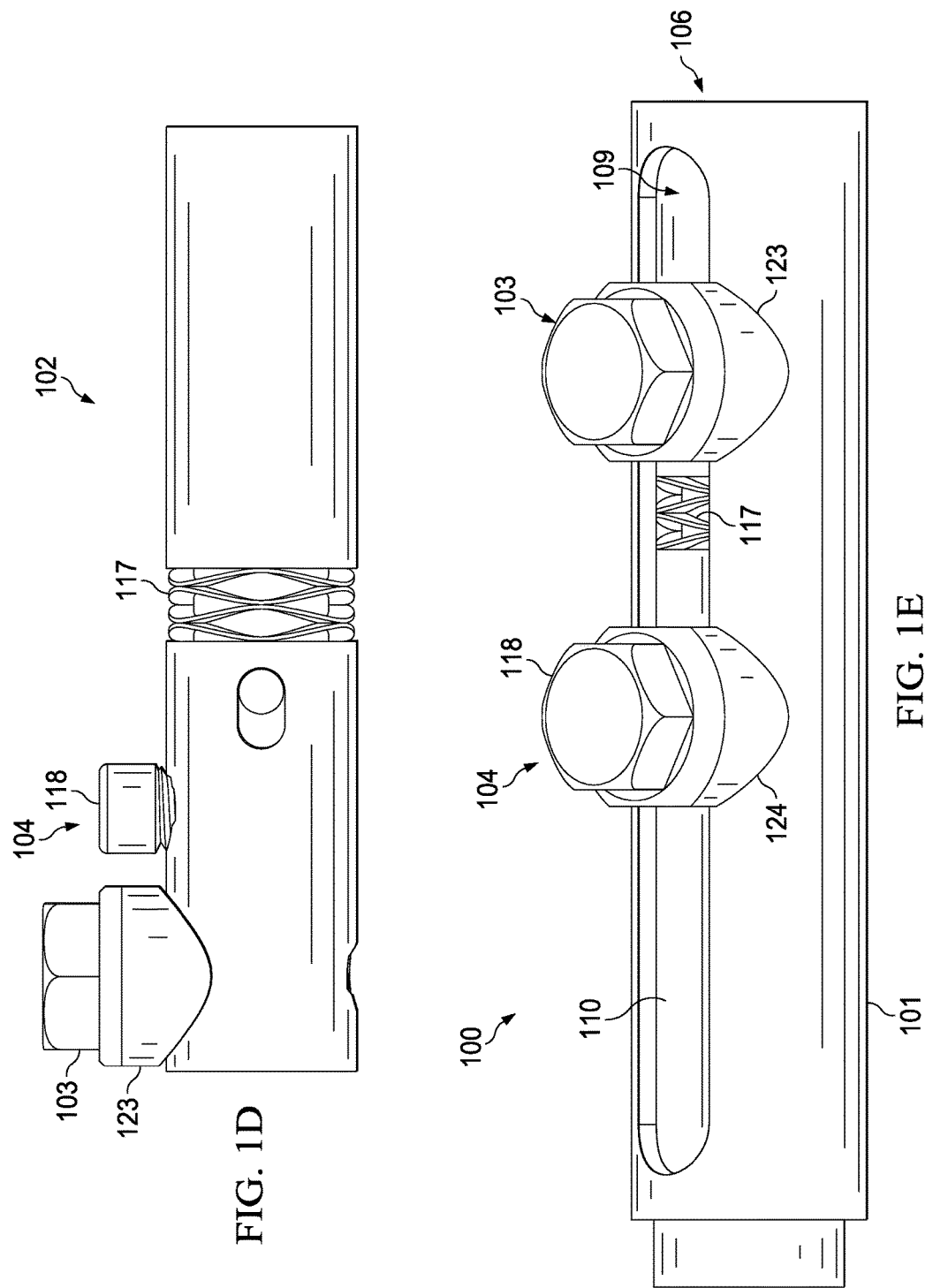

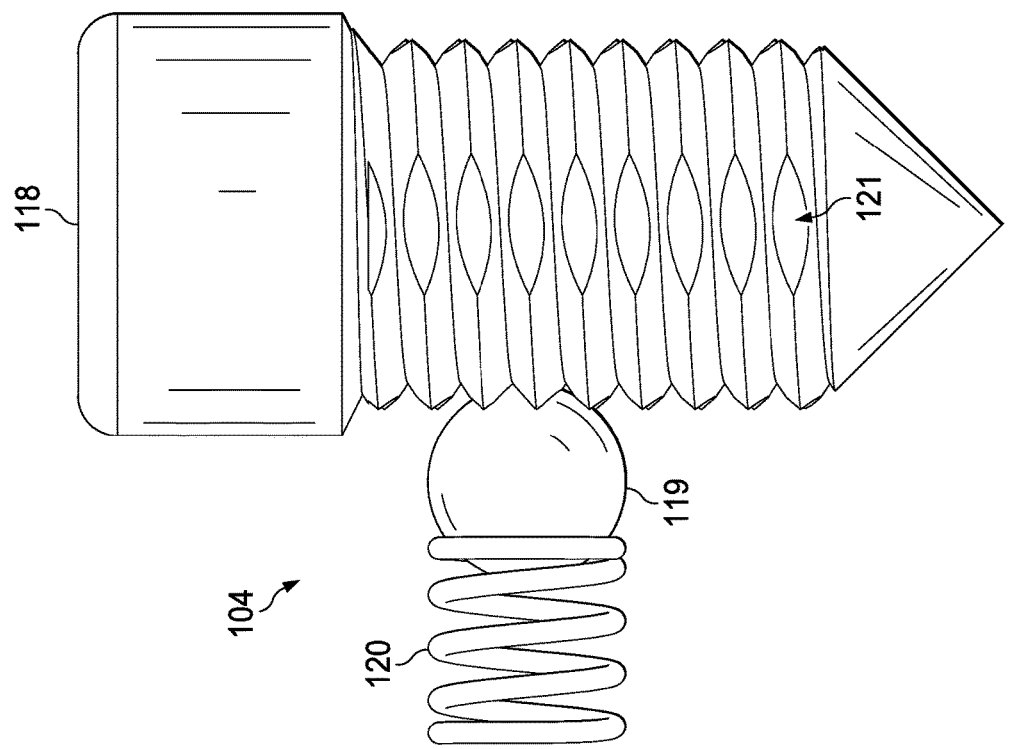

DYNAMIZATION MODULE FOR EXTERNAL FIXATION STRUT

This is a continuation application of U.S. application Ser. No. 14/260,134, which was filed on Apr. 23, 2014 and is incorporated herein by reference in its entirety.

TECHNICAL FIELD

The present disclosure relates in general to the field of external fixation, and more specifically, to dynamization modules for external fixation struts.

BACKGROUND OF THE DISCLOSURE

Without limiting the scope of the disclosure, this background is described in connection with external fixation devices and specifically connection struts and rods. Generally, external fixation devices are commonly used in a variety of surgical procedures including limb lengthening, deformity correction, fracture reduction, and treatment of non-unions, mal-unions, and bone defects. The process involves a rigid framework comprising several rings that are placed externally around the limb and attached to bone segments using wires and half pins, which are inserted into the bone segments and connected to the related section of the external rigid framework. The opposite rings of the rigid framework are interconnected by either threaded or telescopic rods directly or in conjunction with uni-planar or multi-planar hinges, which allow the surgeon to connect opposite rings that are not parallel to each other after manipulation with bone segments either rapidly (acutely) or gradually over a period of time.

For example, in bone fracture reduction or non-union treatment, the wires and half pins are inserted into each bone segment and attached to rings of a rigid framework. The rigid framework is used to acutely reduce a displacement and restore alignment between the bone segments. During the realignment of the bone segments, the orientations of opposite rings are often not parallel. Those opposite rings of the rigid framework are connected together by threaded or telescopic rods with attached uni-planar or multi-planar hinges. This allows the opposite bone segment to be rigidly fixed until complete fracture healing or bone consolidation is completed.

Also for example, in limb lengthening, the bone is surgically divided into two segments and wires and half pins are inserted into bone segments above and below the surgical bone cut and attached to rings of a rigid framework interconnected by struts or telescopic connection rods. The rigid framework is used to gradually push the two bone segments apart longitudinally over a period of time (e.g., one millimeter a day), which allows the bone to gradually form in the gap between bone segments created by this distraction technique. Once the desired amount of lengthening is achieved (e.g., 5-6 cm), the external apparatus is stabilized into a fixed position and left on the bone segments until mineralization of the newly formed bone is complete (e.g., 3-6 months, depending on the nature of pathology and amount of lengthening).

Similarly, in deformity correction, the bone is surgically divided (usually at the apex of the deformity) into two segments, and wires and half pins are inserted into bone segments above and below the surgical bone cut and attached to rings of a rigid framework. Opposite rings of the rigid framework are connected together by threaded rods with attached uni-planar or multi-planar hinges and an angular distractor is used to gradually push the two bone segments apart angularly over a period of time.

For various bone treatments, introducing controlled destabilization can accelerate bone healing and significantly improve the strength of the fracture callus. Gradually increasing a load is an important part of the bone healing process. To achieve such controlled destabilization, the external fixation devices can be dynamized or minimized There are many ways of achieving dynamization, examples including, for a unilateral fixator, removing its bars, sliding the bars further away from the bone, removing its pins, and/or releasing tension or compression from the system, and for a circular frame, removing its wires, releasing tension from the wires, removing its connection rods between rings, removing the rings from a ring block, and/or releasing tension or compression from the system. These techniques can be problematic since they often result in wide variations in the level of instability and may not effectively limit the dynamization to a desired direction or axis of movement.

One common fixation device is a circular metal structure known as the Ilizarov Apparatus. The Ilizarov Apparatus, when used for limb lengthening or deformity correction, consists of several rings or arches that are placed externally around the limb and attached with wires and half pins to surgically separated bone segments. For limb lengthening, the opposite rings are interconnected directly by three or four threaded or telescopic rods that are regularly adjusted in length for gradual separation of bone segments longitudinally. For angular deformity correction, the opposite rings of the Ilizarov apparatus are connected by a pair of hinges that provide an axis of rotation for the bone segments and an angular distractor that gradually pushes apart two rings and associated bone segments.

Another common external fixation device is the Taylor Spatial Frame, which is a hexapod type external fixation device based on a Stewart platform but shares many components and features of the Ilizarov Apparatus. The Taylor Spatial Frame consists of two external fixation rings attached to bone segments by wires and half pins and connected together by six telescopic struts with multi-planar hinges located at both ends of the strut. Each strut may be lengthened or shortened as necessary to either pull two interconnected ring segments towards each other or push them apart. Adjustment of strut length allows manipulation of the bone segments acutely or gradually in six axes (e.g., lengthening/shortening external/internal rotation, anterior/posterior horizontal translation, medial/lateral horizontal translation, anterior/posterior angular translation, and medial/lateral angular translation) to perform limb lengthening and correct angular, translation and rotational deformities simultaneously.

The Taylor Spatial Frame includes a plurality of struts interconnecting a pair of rings. The wires, half pins, struts and other connection and assembly elements of the frame are connected to the rings via apertures. All of the apertures or holes are located on the same ring surfaces extending from the upper ring surface to the lower ring surface. This creates a positioning problem for wire and half pin attachment and placement of additional connection rods and assembly elements due to the competition for apertures in the fixation ring of the frame or the wires and pins interfering with the connections of the struts to the apertures.

Each strut of the Taylor Spatial Frame has a threaded rod partially disposed inside of a hollow shaft, and the hollow shaft includes an adjustment nut that mates with the threaded rod. To effect either a coarse adjustment (rapid strut length adjustment) or a fine adjustment (gradual strut length adjustment) to the length of the strut, the same threaded rod is pulled out or pushed in relation to the hollow shaft. Because the threaded rod has a finite length, however, using the same threaded rod for rapid strut length adjustment limits the total length of threaded rod available for gradual strut length adjustment during, for example, limb lengthening and deformity correction. As a result, a time consuming exchange of the struts for longer ones during the treatment is required.

Additionally, the replacement or removal of a strut from the Taylor Spatial Frame during the course of treatment is impossible without using external support or other stabilization mechanism to support the rest of frame. The struts of the Taylor Spatial Frame must be connected at the top or bottom of the rings. Such connections require the use of either ball joints in the apertures of the rings or universal joints extending from the top or bottom surfaces of the rings. The Taylor Spatial Frame, however, does not include any locking mechanism for temporarily locking the universal joints or ball joints in their orientation. As a result, if one strut is removed from the frame, it would become unstable and collapse.

SUMMARY

The present disclosure relates, according to some embodiments, to a strut having a longitudinal axis defined therein, the strut comprising a strut housing having a housing adjustment aperture and at least a partial axial bore defined therethrough and an adjustment sleeve slidably disposed within the axial bore of the strut housing. In an embodiment, the adjustment sleeve comprises a first and a second bore extending from a top surface towards a bottom surface of the adjustment sleeve, a first sleeve member having a proximal end, a distal end, and at least a partial axial bore extending from the distal end towards the proximal end, a second sleeve member adjoining the first sleeve member, wherein the second sleeve member comprises a body having an annular surface that is substantially proximal to the distal end of the first sleeve member, the second sleeve member having a beveled end that is slidably disposed within the axial bore of the first sleeve member, and a biasing mechanism positioned between the first sleeve member and the second sleeve member.

In an embodiment, the strut further comprises a fastener that releasably couples the strut housing to the adjustment sleeve, wherein the fastener extends from the housing adjustment aperture to the first bore. In an embodiment, the strut further comprises an adjustment mechanism that comprises an element that passes through the second bore and comes in contact with the beveled end of the second sleeve member. In an embodiment, adjusting the element changes a vertical position of the element in relation to the adjustment sleeve and is thereby operable to control a longitudinal displacement of the beveled end that is in contact with the element and is slidably disposed within the axial bore of the first sleeve member.

In an embodiment, the element may be in one of a first position and a second position, wherein in the first position, the element is tightened so that relative movement between the first sleeve member and the second sleeve member is minimized, and wherein in the second position, the element is loosened so that there is relative movement between the first sleeve member and the second sleeve member.

In an embodiment, if the element is in the first position, the beveled end is in a distal position, and if the element is in the second position, the beveled end is in a proximal position, wherein the distal position is longitudinally placed further away than the proximal position from the axial bore of the first sleeve member.

In an embodiment, if the beveled end is in the distal position, the biasing mechanism becomes less active, and if the beveled end is in the proximal position, the biasing mechanism becomes more active.

In an embodiment, the adjustment mechanism is positioned between the fastener and the biasing mechanism. In another embodiment, the biasing mechanism is positioned between the fastener and the adjustment mechanism.

In an embodiment, the first and second bores are positioned on the first sleeve member. In another embodiment, the first bore is positioned on the first sleeve member, and the second bore is positioned on the second sleeve member.

In an embodiment, the element comprises a plurality of longitudinal grooves on an outer surface of the element. In an embodiment, the adjustment mechanism further comprises a ball coupled with a second biasing member, wherein when the element is turned, the ball can releasably latch into one of the plurality of longitudinal grooves of the element. In an embodiment, the longitudinal placement of the beveled end of the second sleeve member can be quantifiably adjusted by turning the element from a first latched position to a second latched position.

In an embodiment, the first and the second bores are internally threaded radial bores. In an embodiment, the first bore traverses the adjustment sleeve. In an embodiment, the biasing mechanism between the first sleeve member and the second sleeve member is positioned between the distal end of the first sleeve member and the body of the second sleeve member. In an embodiment, the biasing mechanism is selected from at least one of a spring, coiled spring, tension/extension spring, compression spring, torsion spring, constant spring, variable spring, flat spring, machined spring, cantilever spring, helical spring, compression spring, volute spring, tension or extension spring, hairspring or balance spring, leaf spring, V-spring, belleville spring, a constant-force spring, gas spring, mainspring, progressive rate coil spring, spring washer, torsion spring, or a wave spring.

The present disclosure relates, according to some embodiments, to an adjustment sleeve that may be slidably disposed within an axial bore of a strut housing. In an embodiment, the adjustment sleeve comprises a first and a second bores extending from a top surface to a bottom surface of the adjustment sleeve, a first sleeve member having a proximal end, a distal end, and at least a partial axial bore extending from the distal end towards the proximal end, and a second sleeve member adjoining the first sleeve member, wherein the second sleeve member comprises a body having an annular surface that is substantially proximal to the distal end of the first sleeve member, and a beveled end that is slidably disposed within the axial bore of the first sleeve member.

In an embodiment, the adjustment sleeve comprises a biasing mechanism between the first sleeve member and the second sleeve member positioned between the first sleeve member and the second sleeve member.

In an embodiment, the adjustment sleeve comprises an adjustment mechanism that comprises an element that passes through the second bore and comes in contact with the beveled end of the second sleeve member. In an embodiment, adjusting the element changes a vertical position of the element in relation to the adjustment sleeve and is thereby operable to control a longitudinal displacement of the beveled end that is slidably disposed within the axial bore of the first sleeve member and is in contact with the element.

In an embodiment, the present invention also includes a method of assembling a strut having a longitudinal axis defined therethrough. In an embodiment, the method comprises providing a strut housing having a housing adjustment aperture and at least a partial axial bore defined therethrough and providing an adjustment sleeve slidably disposed within the axial bore of the strut housing. In an embodiment, the adjustment sleeve comprises a first and a second bores extending from a top surface towards a bottom surface of the adjustment sleeve, a first sleeve member having a proximal end, a distal end, and at least a partial axial bore extending from the distal end towards the proximal end, and a second sleeve member adjoining the first sleeve member. In an embodiment, the second sleeve member comprises a body having an annular surface that is substantially proximal to the distal end of the first sleeve member, the second sleeve member having a beveled end that is slidably disposed within the axial bore of the first sleeve member, and a biasing mechanism positioned between the first sleeve member and the second sleeve member. In an embodiment, the method further comprises releasably coupling the strut housing with the adjustment sleeve with a fastener, wherein the fastener extends from the housing adjustment aperture to the first bore. In an embodiment, the method further comprises controlling, with an adjustment member, a longitudinal placement of the beveled end that is slidably disposed within the axial bore of the first sleeve member, wherein the adjustment mechanism comprises an element that passes through the second bore and comes in contact with the beveled end of the second sleeve member, wherein adjusting the element changes a vertical position of the element in relation to the adjustment sleeve.

In an embodiment, the method further comprises providing the element in one of a first position and a second position, wherein in the first position, tightening the element so that relative movement between the first sleeve member and the second sleeve member is minimized, and wherein in the second position, loosening the element so that there is relative movement between the first sleeve member and the second sleeve member.

In an embodiment, if the element is in the first position, the beveled end is in a distal position, and if the element is in the second position, the beveled end is in a proximal position, wherein the distal position is longitudinally placed further away than the proximal position from the axial bore of the first sleeve member.

In an embodiment, if the beveled end is in the distal position, the biasing mechanism becomes less active, and if the beveled end is in the proximal position, the biasing mechanism becomes more active.

In another embodiment, the present invention includes a method of adjusting the position of two bone segments. In an embodiment, the method comprises identifying a patient in need of having the position of the two bone segments adjusted and affixing an external fixation frame to the two bone segments. In an embodiment, the external fixation frame comprises two or more fixation plates or rings. In an embodiment, the method further comprises connecting the two or more fixation plates or rings of the external fixation frame with one or more struts that provide for bone dynamization, each of the one or more struts having a longitudinal axis defined therein, the strut comprising: a strut housing having a housing adjustment aperture and at least a partial axial bore defined therethrough; an adjustment sleeve slidably disposed within the axial bore of the strut housing, the adjustment sleeve comprising: first and second bores extending from a top surface towards a bottom surface of the adjustment sleeve; a first sleeve member having a proximal end, a distal end, and at least a partial axial bore extending from the distal end towards the proximal end; a second sleeve member adjoining the first sleeve member, wherein the second sleeve member comprises a body having an annular surface that is substantially proximal to the distal end of the first sleeve member, the second sleeve member having a beveled end that is slidably disposed within the axial bore of the first sleeve member; and a biasing mechanism positioned between the first sleeve member and the second sleeve member; a fastener that releasably couples the strut housing to the adjustment sleeve, wherein the fastener extends from the housing adjustment aperture to the first bore; and an adjustment mechanism that comprises an element that passes through the second bore and comes in contact with the beveled end of the second sleeve member, wherein adjusting the element changes a vertical position of the element in relation to the adjustment sleeve and is thereby operable to control a longitudinal displacement of the beveled end that is in contact with the element and is slidably disposed within the axial bore of the first sleeve member; and adjusting an amount of dynamization of the strut to maximize the strength of bone growth between the two bone segments during bone remodeling.

In an embodiment, the two or more bone segments are the result of at least one of lengthening surgery, angular alignment surgery, or an accidental break in the bone.

BRIEF DESCRIPTION OF THE DRAWINGS

Embodiments are illustrated by way of example in the accompanying figures, in which like reference numbers indicate similar parts, and in which:

FIG. 1D is a side view of an adjustment sleeve with a fastener and an adjustment mechanism according to an embodiment of the present disclosure.

FIG. 1E is a perspective view of a strut according to an embodiment of the present disclosure.

FIG. 1H is a side view of an adjustment mechanism comprising a ball, biasing mechanism, and element according to an embodiment of the present disclosure.

DETAILED DESCRIPTION

While making and using of various embodiments of the present disclosure are discussed in detail below, it should be appreciated that the present disclosure provides many applicable inventive concepts that can be embodied in a wide variety of specific contexts. The specific embodiments discussed herein are merely illustrative of specific ways to make and use the disclosure and do not limit the scope of the disclosure.

To facilitate the understanding of this disclosure, a number of terms are defined below. Terms defined herein have meanings as commonly understood by a person of ordinary skill in the areas relevant to the present disclosure. Terms such as "a", "an", and "the" are not intended to refer to only a singular entity, but include the general class of which a specific example may be used for illustration. The terminology herein is used to describe specific embodiments of the disclosure, but their usage does not limit the disclosure, except as outlined in the claims.

The present disclosure relates generally to an external fixation strut with a housing that allows for rapid and gradual adjustment in length and an adjustment sleeve that allows for further adjustment in length of the strut and biasing of its adjustment sleeve. The fine adjustment to the overall length of the strut allows for highly controlled bone dynamization with a great improvement in the final strength of the bone. The biasing can be varied both in length and flexibility to maximize the bone dynamization based on, e.g., the type of bone break or separation, the bone being reformed or grown, the position of the bone break or separation, the gender, age, weight, metabolism of the patient, if the patient is taking other drugs or receiving therapies that could accelerate or reduce bone reformation, growth, calcination. The controllable biasing of the strut's adjustment sleeve provides a degree of longitudinal flexibility in the strut. This controllable flexibility in the strut allows an external fixation device to provide proper amount of stabilization at different stages of a patient's healing process. For example, when using an external fixation device on fractured bones, the external fixation device needs to be stable to prevent movement of the fractured bones that may cause deformity. However, if the external fixation device is too stable, at times, that may have its own disadvantages. When a callous begins to form on the fractured bones, destabilizing the external fixation device in a controlled fashion may have several advantages. An advantage of such destabilization is exerting sufficient loading force and pressure to the patient's body part (i.e., leg) to accelerate the healing process. It is preferable if the loading process is controlled. Preferably, the loading process proceeds gradually during the mineralization phase of the fracture healing process. This will result in accelerated bone healing and in a stronger union of the fractured tissues.

Figure 1A:
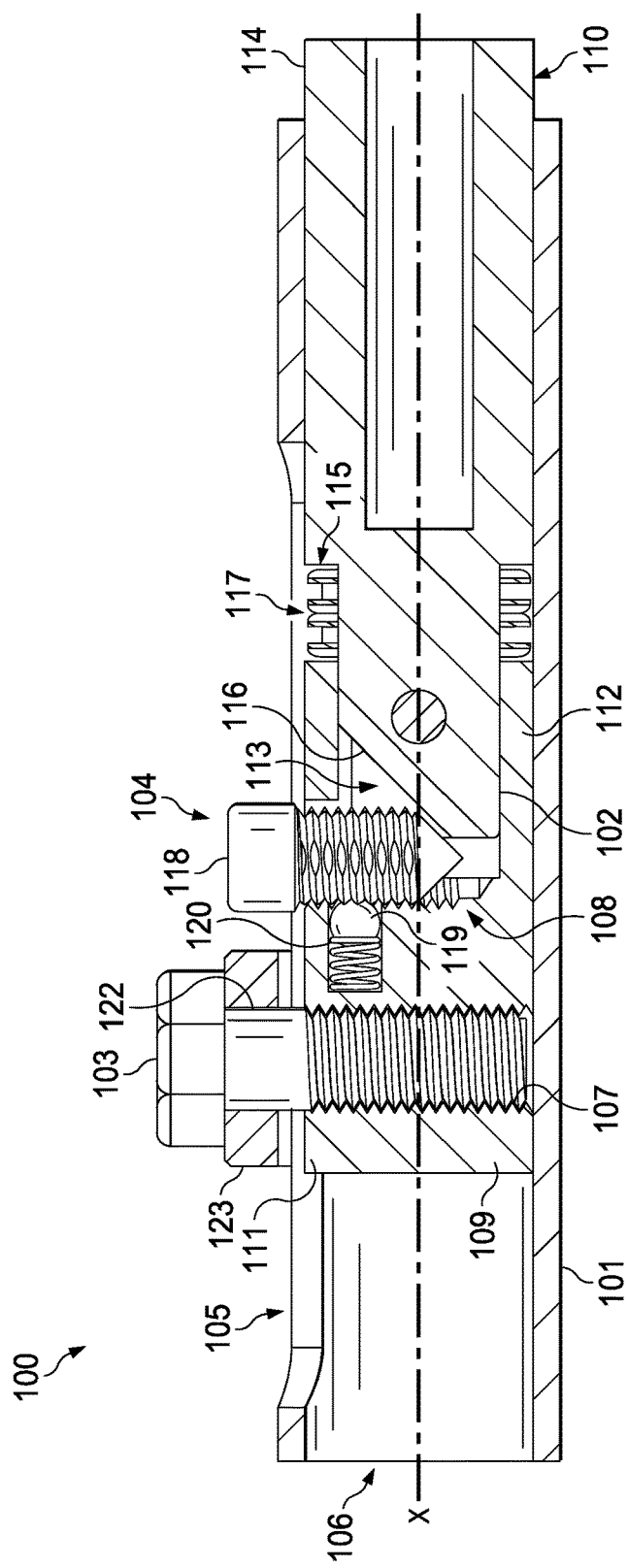
FIG. 1A is a cutaway view of a strut according to an embodiment of the present disclosure.
Figure 1B:
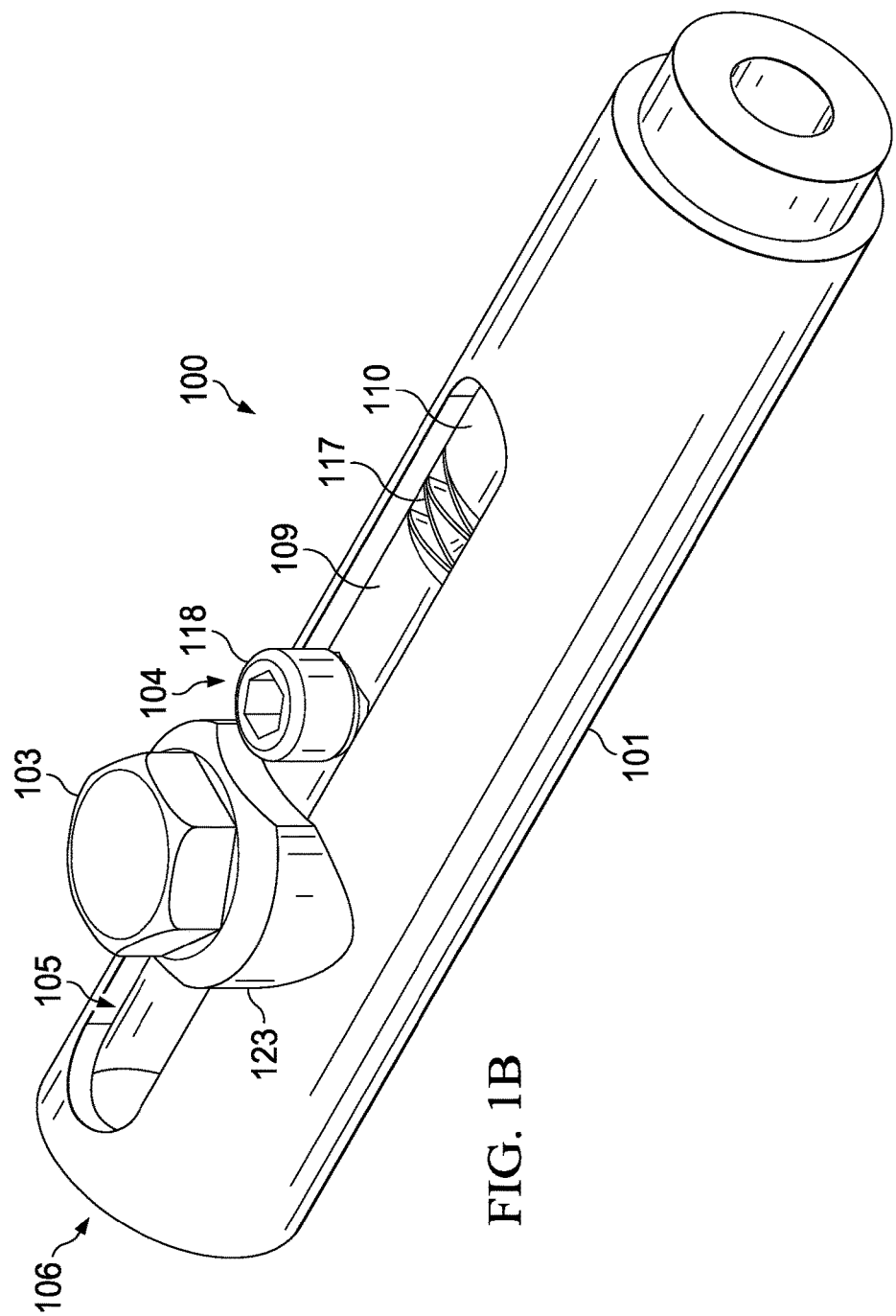
FIG. 1B is a perspective view of a strut according to an embodiment of the present disclosure.
Figure 1C:
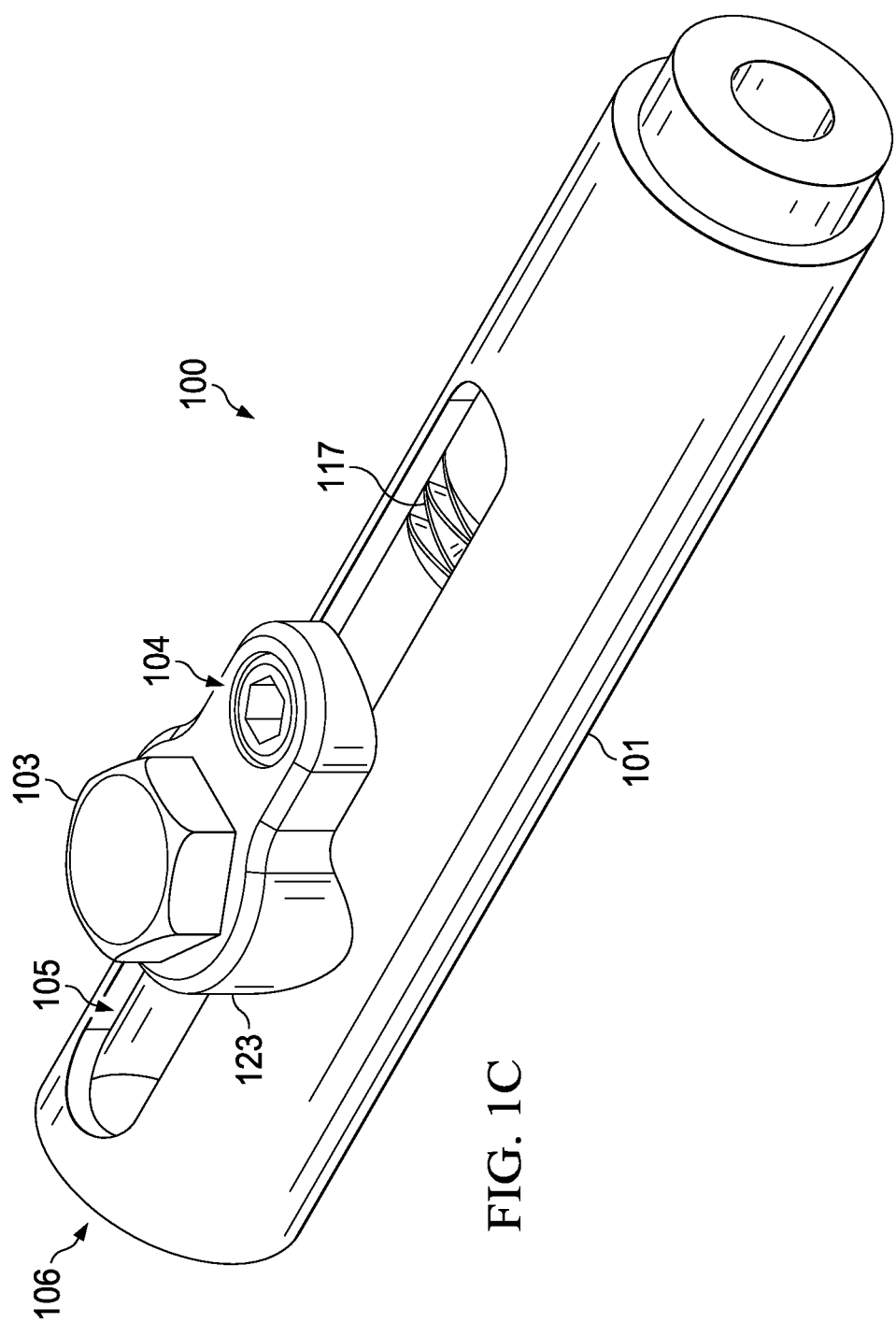
FIG. 1C is another perspective view of a strut according to an embodiment of the present disclosure.

FIGS. 1A-1B are a cutaway view and a perspective view, respectively, of an embodiment of an external fixation strut of the present disclosure. In FIGS. 1A-1B, the external fixation strut 100 has a longitudinal axis X defined therein and comprises a strut housing 101, an adjustment sleeve 102, a fastener 103, a conformal washer 123, and an adjustment mechanism 104. While FIGS. 1A-1B illustrate an embodiment where the fastener 103 and the adjustment mechanism 104 are separate components, in other embodiments, as illustrated in FIG. 1C, the fastener 103 and the adjustment mechanism 104 may be connected. In this embodiment, the conformal washer 123 connects the fastener 103 and the adjustment mechanism 104. Here, the conformal washer 123 limits or prevents the adjustment mechanism 104, and more specifically its element 118 (explained later), from getting detached from the adjustment sleeve 102.

In an embodiment, the strut housing 101 comprises a housing adjustment aperture 105 in a wall of the strut housing 101. Length and size of the housing adjustment aperture 105 may vary depending on the intended degree of possible lengthening of the strut. In an embodiment, the longer the housing adjustment aperture 105, the greater the degree of the strut's 100 lengthening. The housing adjustment aperture 105 also serves as a window to allow positioning and referencing the adjustment sleeve 102 to aid in the adjustment of the end-to-end length of the strut 100 in a rapid manner. The strut housing 101 also comprises an axial bore 106 defined therethrough. In an embodiment, the axial bore 106 may be a partial axial bore, while in another embodiment, the axial bore 106 may be a full axial bore.

In an embodiment, the adjustment sleeve 102 may be slidably disposed within the axial bore 106 of the strut housing 101. The adjustment sleeve 102 is slidable within the axial bore 106 to allow adjustment of the end-to-end length of the strut 100 in a rapid manner. In an embodiment, the adjustment sleeve 102 comprises a first bore 107 and a second bore 108, both extending from a top surface of the adjustment sleeve 102 towards a bottom surface of the adjustment sleeve 102. The fastener 103 is inserted through a conformal washer aperture 122 centrally defined in the conformal washer 123, through the adjustment aperture 105 in the strut housing 101, and through the first bore 107 to secure the adjustment sleeve 102 to the strut housing 101. The conformal washer 123 can have a variety of configurations to provide various design advantages. In some embodiments, the conformal washer 123 has a smooth inner surface. In other embodiments, the inner surface of the conformal washer 123 has a teethed portion cooperating with a matching teethed portion of the strut housing 101 to provide a more secured connection with the strut housing 101. In an embodiment, the conformal washer aperture 122 is a threaded radial bore. In an embodiment, the conformal washer 123 and the fastener 103 may form a single body, while in another embodiment, the conformal washer 123 may be an independent single unit.

In an embodiment, the strut housing 101 may have graduation marks (not shown) indicating the lengths of the strut 100 as a relative value. The graduation marks do not necessarily have to be based on a traditional measuring system, or indicate the effective length of the strut 100 at all. For instance, the graduation marks could indicate the percentage of total strut extension, or daily increments for cases where the translation takes place over an extended period of time. Reference to a neutral position can be useful to set the base members at a predetermined "neutral" position.

The adjustment sleeve 102 comprises a first sleeve member 109 and a second sleeve member 110. The first sleeve member 109 comprises a proximal end 111, a distal end 112, and at least a partial axial bore 113 extending from the distal end 112 towards the proximal end 111 of the first sleeve member 109. The second sleeve member 110 adjoins the first sleeve member 109 and comprises a body 114 having an annular surface 115 that is substantially proximal to the distal end 112 of the first sleeve member 109. The second sleeve member 110 further comprises a beveled end 116 that is slidably disposed within the axial bore 113 of the first sleeve member 109. The adjustment sleeve 102 also comprises a biasing mechanism 117 between the first sleeve member 109 and the second sleeve member 110. In an embodiment, the biasing mechanism 117 may be a spring, coiled spring, tension/extension spring, compression spring, torsion spring, constant spring, variable spring, flat spring, machined spring, cantilever spring, helical spring, compression spring, volute spring, tension or extension spring, hairspring or balance spring, leaf spring, V-spring, belleville spring, a constant-force spring, a gas spring, a mainspring, progressive rate coil spring, spring washer, torsion spring, wave spring, pneumatic cylinder/piston arrangements, lengths of resilient material such as rubber or other elastic material. The biasing mechanism 117 can be made from a variety of materials that will provide varying compression, flexion, stabilization, rotational, or other forces by using, alone or in combination, a wide variety of materials, including but not limited to, steel, titanium, aluminum, chromium, copper, bronze, metal alloys, wood, plastic, polymers, latex, nylon, polypropylene, polystyrene, polyurethane, ceramics, or rubber. In other embodiments, the biasing mechanism 117 may be any component that compresses, thereby providing biasing between the first sleeve member 109 and the second sleeve member 110. A side view of an embodiment of just the adjustment sleeve 102 with the fastener 103, the conformal washer 123, and the adjustment mechanism 104 is provided in FIG. 1D.

In an embodiment, the fastener 103 releasably couples the strut housing 101 with the adjustment sleeve 102. The fastener 103 extends through the conformal washer aperture 122 centrally defined in the conformal washer 123, the housing adjustment aperture 105, and the first bore 107. In an embodiment, the fastener 103 may be rotationally disposed in the conformal washer 123 and the first bore 107. In an embodiment, the fastener 103 may be a screw or a sleeve fastener. In an embodiment, the fastener 103 may be threaded. In an embodiment, the fastener 103 may be an anchor bolt, machine screw, thread cutting machine screw, sheet metal screw, hex bolt, carriage bolt, lag bolt, socket screw, shoulder bolt, fastening mechanism that employs one of the aforementioned types, or any other fastening mechanism that allows the fastener 103 to couple the strut housing 101 with the adjustment sleeve 102. In an embodiment, the first bore 107 and the second bore 108 may be internally threaded radial bores.

In an embodiment, the adjustment mechanism 104 comprises an element 118 that passes through the second bore 108 of the adjustment sleeve 102. The element 118 may be rotatably disposed in the second bore 108. The distal end of element 118 comprises an angled tip that comes in contact with the beveled end 116 of the second sleeve member 110, wherein adjusting the element 118 changes a vertical position of the element 118 in relation to the adjustment sleeve 102. This adjustment mechanism 104, and more specifically the element 118, thereby is operable to control a longitudinal displacement of the beveled end 116 that comes in contact with the element 118 and is slidably disposed within the axial bore 113 of the first sleeve member 109. In an embodiment, the element 118 may be a rotation element such as a bolt or threaded screw. In other embodiments, the element 118 may come in other configurations that allow the adjustment of the longitudinal displacement of the beveled end 116. In an embodiment, the element 118 comprises a plurality of longitudinal grooves (not shown) on an outer surface of the element 118.

In an embodiment, the element 118 may be in one of a first position or a second position. In the first position, the element 118 is tightened so that the second sleeve member 110 is maximally displaced from the first sleeve member 109. In this arrangement, relative movement between the first sleeve member 109 and the second sleeve member 110 is minimized. In the second position, the element 118 is loosened, which allows relative movement between the first sleeve member 109 and the second sleeve member 110. The element 118 can be positioned along its entire length in 1, 2, 3, 4, 5, 6, 7, 8, 9, 10, 11, 12, 13, 14, 15, 16, 17, 18, 19, 20, 25, 30, 35, 40, 45, 50 or more positions. In some embodiment, the various positions may be calibrated to match a certain level of displacement, e.g., one change in position could alter the length of the displacement from 0.1, 0.5, 1.0, 1.5, 2.0, 2.5, 3.0, 4.0, 5.0, 6.0, 7.0, 7.5, 8.0, 9.0, 10.0, 100, 200, 250, 300, 400, 500, 600, 700, 750, 800, 900, or 1,000 microns, or even, 0.1, 0.2, 0.3, 0.4, 0.5, 0.6, 0.7, 0.8, 0.9 or even 1.0 mm. In this embodiment, if and/or when the element 118 is in the first position, the beveled end 116 is in a distal position, and if and/or when the element 118 is in the second position, the beveled end 116 is in a proximal position, wherein the distal position is longitudinally placed further away than the proximal position from the axial bore of the first sleeve member. In this embodiment, when the beveled end 116 is in the distal position, the biasing mechanism 117 becomes less active, thereby providing more stability to the strut 100 and to the overall external fixation device. And when the beveled end 116 is in the proximal position, the biasing mechanism 117 becomes more active, thereby permitting some limited movement in the strut 100 and to the overall external fixation device. As previously discussed, there are several advantages to being able to control the movement or stabilization of the strut and the overall external fixation device.

In sum, in this embodiment, when the element 118 is tightened and is in the first position, the beveled end 116 is driven further away from the first sleeve member 109, and the second sleeve member 110 is extended away from the first sleeve member 109. This causes the biasing mechanism 117 placed between the first sleeve member 109 and the second sleeve member 110 to become less active as the gap between the first and second sleeve members 109, 110 widens. When the element 118 is loosened and is in the second position, the beveled end 116 is placed closer to the first sleeve member 109, and the second sleeve member 110 is less extended away from the first sleeve member 109. The biasing mechanism 117 thus becomes more active as more play is introduced between the first and second sleeve members 109, 110.

In an embodiment, the adjustment mechanism 104 may further comprise a ball 119 coupled with a second biasing member 120. A close up view of this adjustment mechanism 104 is provided in FIG. 1H. In this embodiment, the element 118 comprises a plurality of longitudinal grooves 121 on an outer surface of the element 118. The adjustment mechanism 104 further comprises the ball 119 coupled with the second biasing member 120. Here, when the element 118 is turned, the ball 119 releasably latches into one of the plurality of longitudinal grooves 121 of the element 118.

In an embodiment, a longitudinal placement of the beveled end 116 of the second sleeve member 110 can be quantifiably adjusted by turning the element 118 from a first latched position to a second latched position. In an embodiment, when the ball 119 latches into one of the plurality of longitudinal grooves 121 of the element 118, a user can feel and/or hear a click, thereby facilitating the quantifiable adjustment of the beveled end 116 of the second sleeve member 110. The ball 119 coupled with the second biasing member 120 therefore allows a user (i.e., doctor or patient) to be able to control the level of play in the strut and the overall level of movement and stability in the external fixation device.

Figure 1F:
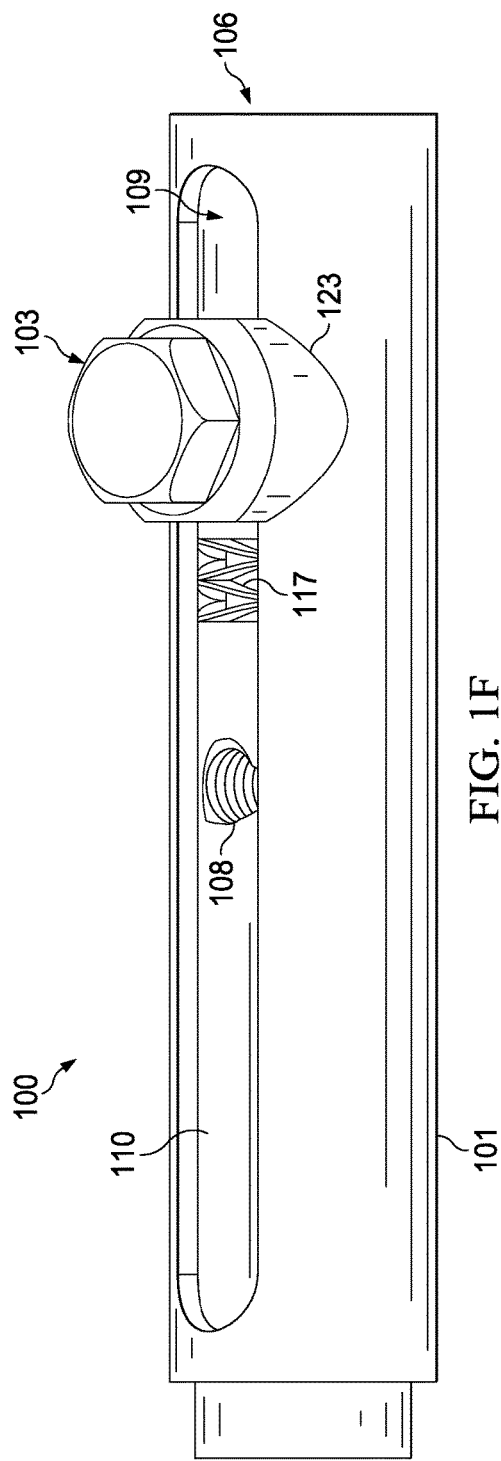
FIG. 1F is another perspective view of a strut according to an embodiment of the present disclosure.
Figure 1G:
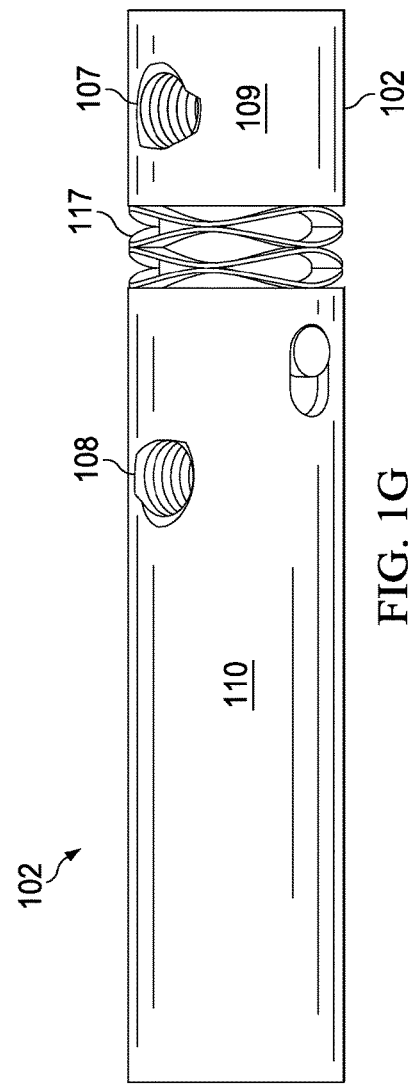
FIG. 1G is a perspective view of an adjustment sleeve according to an embodiment of the present disclosure.

FIGS. 1A-1D illustrate an embodiment of the strut 100 where the adjustment mechanism 104 is positioned between the fastener 103 and the biasing mechanism 117. But in other embodiments, as shown in FIGS. 1E-1G, the biasing mechanism may be positioned between the fastener and the adjustment mechanism. While FIGS. 1A-1D illustrate an embodiment where the first bore 107 and the second bore 108 are positioned on the first sleeve member 109 of the adjustment sleeve 102, in other embodiments, as shown in FIGS. 1E-1G, the first bore and the second bore may be positioned on different sleeve members of the adjustment sleeve.

FIGS. 1E-1F are perspective views of another embodiment of the strut 100. This embodiment has substantially similar components as the embodiment illustrated in FIGS. 1A-1D. Thus, the strut 100 comprises the strut housing 101, adjustment sleeve 102, the fastener 103, the conformal washer 123, and the adjustment mechanism 104. However, in this embodiment, the biasing mechanism 117 is positioned between the fastener 103 and the adjustment mechanism 104. Also, in this embodiment, the first bore 107 and the second bore 108 are positioned on the first sleeve member 109 and the second sleeve member 110 respectively. And also, in this embodiment, the adjustment mechanism 104 comprises its own conformal washer 124.

FIG. 1G is a perspective view of an embodiment of just the adjustment sleeve 102. As shown, in this embodiment, the first sleeve member 109 is shorter than the second sleeve member 110. And the biasing mechanism 117 is positioned between the first bore 107 and the second bore 108. The biasing mechanism 117 would thus be positioned between the fastener 103 and the adjustment mechanism 104.

Figure 2:
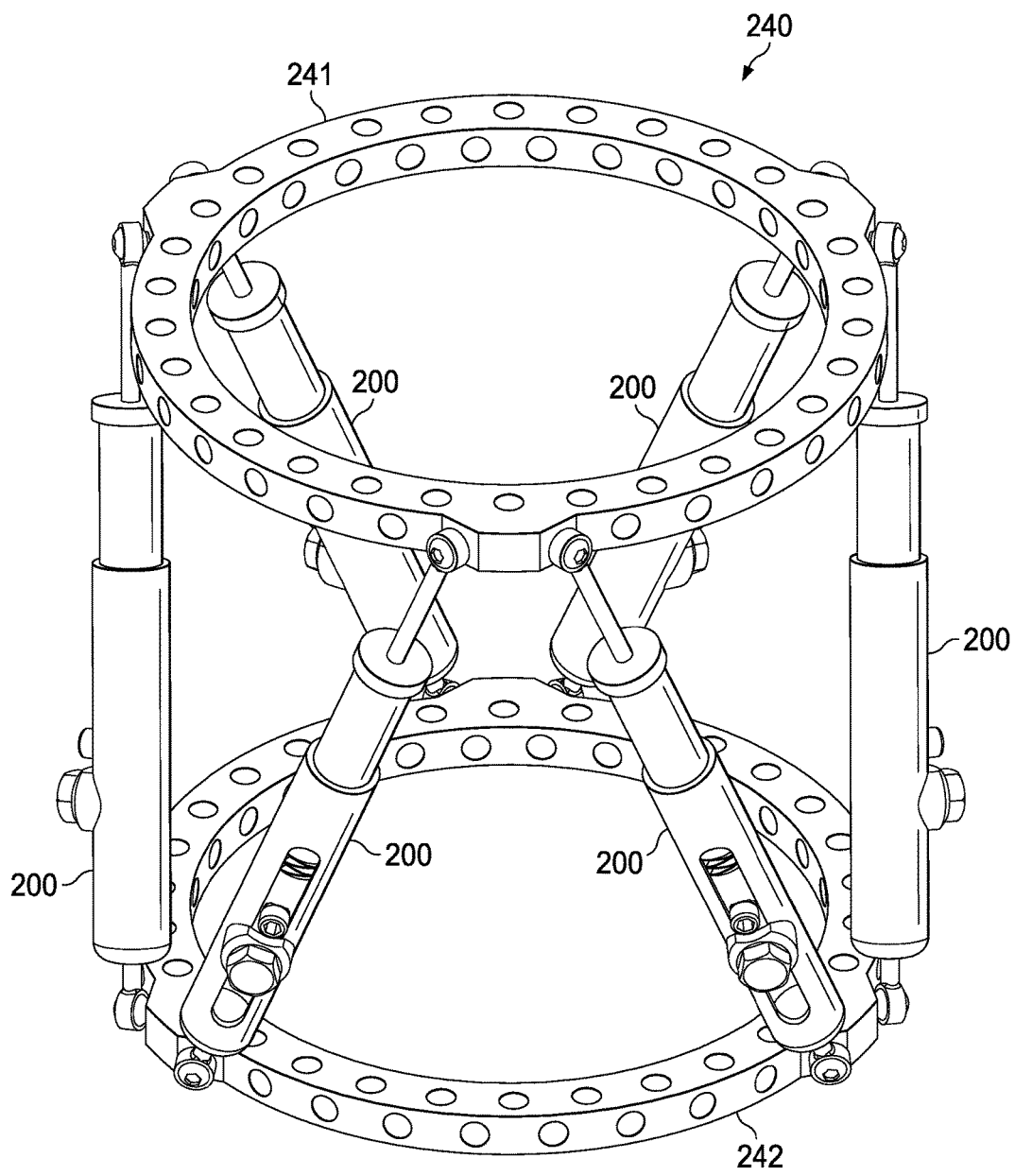
FIG. 2 is a perspective view of an external fixation device comprising external fixation rings and struts according to an embodiment of the present disclosure.

FIG. 2 is a perspective view of an embodiment of an external fixation device 240 employing the struts 200. In this embodiment, the external fixation device 240 comprises six struts 200. The external fixation device 240 comprises a first external fixation ring 241 and a second external fixation ring 242 that surround a bone (not shown). The first external fixation ring 241 and the second external fixation ring 242 are connected by six of the struts 200. The struts 200 may be connected to the external fixation rings 241, 242 by various methods. In an embodiment, each of the struts 200 may comprise a first articulatable ball joint (not shown) attached at each end of the strut 200. In an embodiment, the first articulatable ball joint houses a first ball (not shown). The first ball (not shown) includes a first ball stud (not shown) that passes through a slot (not shown) into a threaded aperture in each of the external fixation rings 241 and 242. While this embodiment shows six of the struts 200, in other embodiments there may be any number of struts. For example, there may be three, four, or five struts.

Since there are multiple struts, it is desirable to be able to uniquely identify each strut so that the strut length adjustments for each strut can be tracked and implemented. An information indicator may be mounted onto or embedded into the struts for identifying the struts. In some embodiments, the information indicator may be a physical identifier, such as inscription, paper, or label of a code, color, or serial number corresponding to relevant information. Examples of the relevant information embodied or represented by the information indicator may include the type of the strut, the maximum or minimum strut length, strut number, etc. In some embodiments, the information indicator may be an electronic identifier. One common method of identification includes a radio frequency (RF) sensor that wirelessly communicates with a radio frequency transmitter (RFID) located on the adjustment mechanism of the strut. Another strut number identifier may include a bar code reader that counts a specific number of grooves on the adjustment mechanism of the strut or communicates with magnetic strip located on the adjustment mechanism of the strut. In another embodiment, strut number identifier includes a sensor that receives information from a touch memory button located on the adjustment mechanism of the strut. In other embodiments, the information indicator may be any other device suitable to embody or represent information or a combination of the types of indicators discussed in the present application.

The methods of the present disclosure may be performed with a subject, e.g., a human or another vertebrate animal. One or more bones (of the subject) to be fixed may be selected. Any suitable bone(s) may be selected, such as a long bone(s) and/or at least a pair of bones connected via an anatomical joint. Exemplary bones include leg bones (femur, tibia, and fibula), arm bones (humerus, radius, and ulna), foot bones (calcaneus, talus, metatarsals, and phalanges), wrist/hand bones (carpals, metacarpals, and phalanges), etc. In exemplary embodiments, one or more bones including at least one long bone may be selected.

An external fixation device may be constructed along and at least partially surrounding the selected bone(s). The external fixation device may include a plurality of rings fixed in position relative to one another by numerous connecting rods or struts secured to the rings.

The external fixation device may be connected to the selected bone(s). Connection may be performed at any suitable time, such as before, during, and/or after construction of the external fixation device. For example, the external fixation device may be assembled and then connected to bone, or individual external fixation device members or external fixation device sub-assemblies may be connected to the bone before the external fixation device is fully assembled. Connection of the external fixation device to bone may include placing connectors, such as wires, pins, screws, and/or rods, among others through the skin and into, through, and/or around the selected bone.

The external fixation device may be reconfigured while it is connected to the one or more selected bones. Reconfiguration may include adjusting the length, angle, position, and/or connection site of one or more external fixation device components, particularly connecting rod. In some embodiments, reconfiguration may involve lengthening and/or shortening one or more (or all) connecting rods of the external fixation device. In some embodiments, reconfiguration may involve replacing one or more connecting rods with a different connecting rod(s). The different connecting rod may be of different size, pivotability, adjustability, shape, and/or the like.

The external fixation device may be braced to facilitate reconfiguration. Bracing the external fixation device may stiffen and/or stabilize the external fixation device such that reconfiguration produces fewer undesired changes to the external fixation device structure as the external fixation device is weakened and altered during reconfiguration. Bracing may be performed by a pair of connecting rods of the external fixation device. In some examples, the brace may be configured to be clipped onto the external fixation device members before the brace is fully secured to the external fixation device members. For example, the brace may include one or more external fixation device engagement elements that are biased to opposingly engage one or more respective external fixation device members. In any case, each engagement element may be secured in place on the external fixation device member by operating a user control, manually or with a tool. Furthermore, the relative spacing and angular disposition of the engagement elements may be fixed by operating a user control, either the same user control(s) for securing the engagement element to a frame member or a distinct user control.

In some examples, the brace may include one or more movable joints, and the brace may be installed in engagement with the external fixation device members with one or more of the joints in a movable configuration. The movable joints then may be adjusted to a locked (fixed) configuration. Alternatively, or in addition, the brace may include a plurality of movable joints and one or more of the movable joints may be locked before or during brace placement onto the frame, and one or more other of the movable joints may be locked after brace placement onto the external fixation device.

The brace may be removed after frame reconfiguration. Accordingly, the brace may be installed with the frame (and connecting rod) fixing bone and removed with the frame reconfigured and still fixing bone. The brace thus may be present on the external fixation device for only a fraction of the time that the external fixation device is fixing bone.

It is contemplated that any embodiment discussed in this specification can be implemented with respect to any method, kit, reagent, or composition of the disclosure, and vice versa. Furthermore, compositions of the disclosure can be used to achieve methods of the disclosure.

Figure 3A:
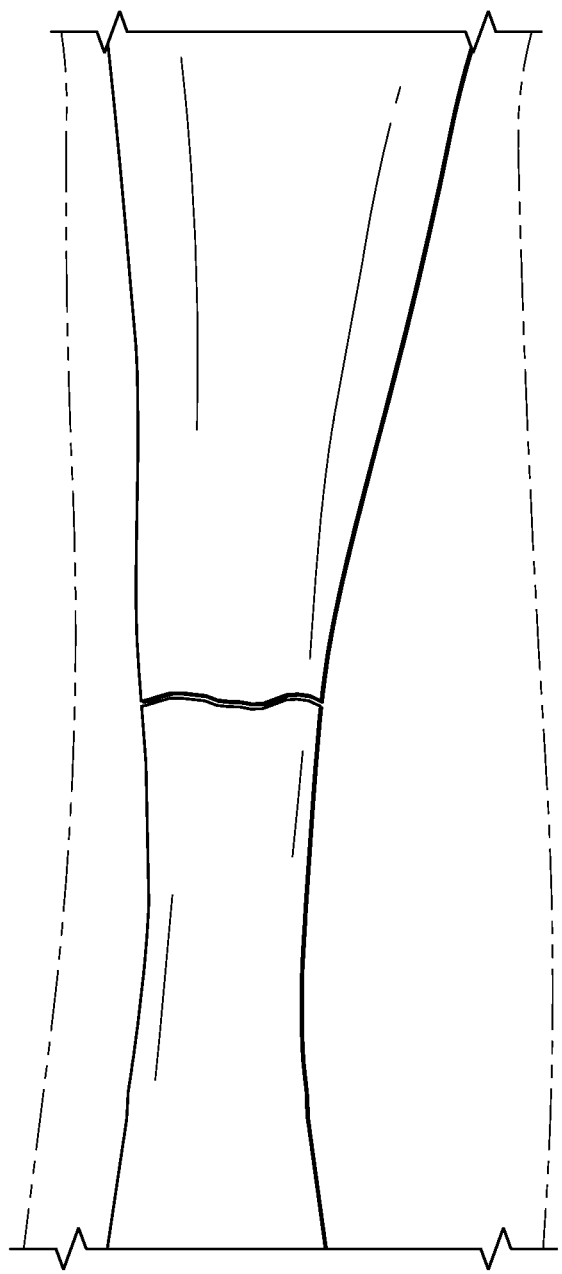
FIG. 3A is a top view of a person's bone.
Figure 3B:
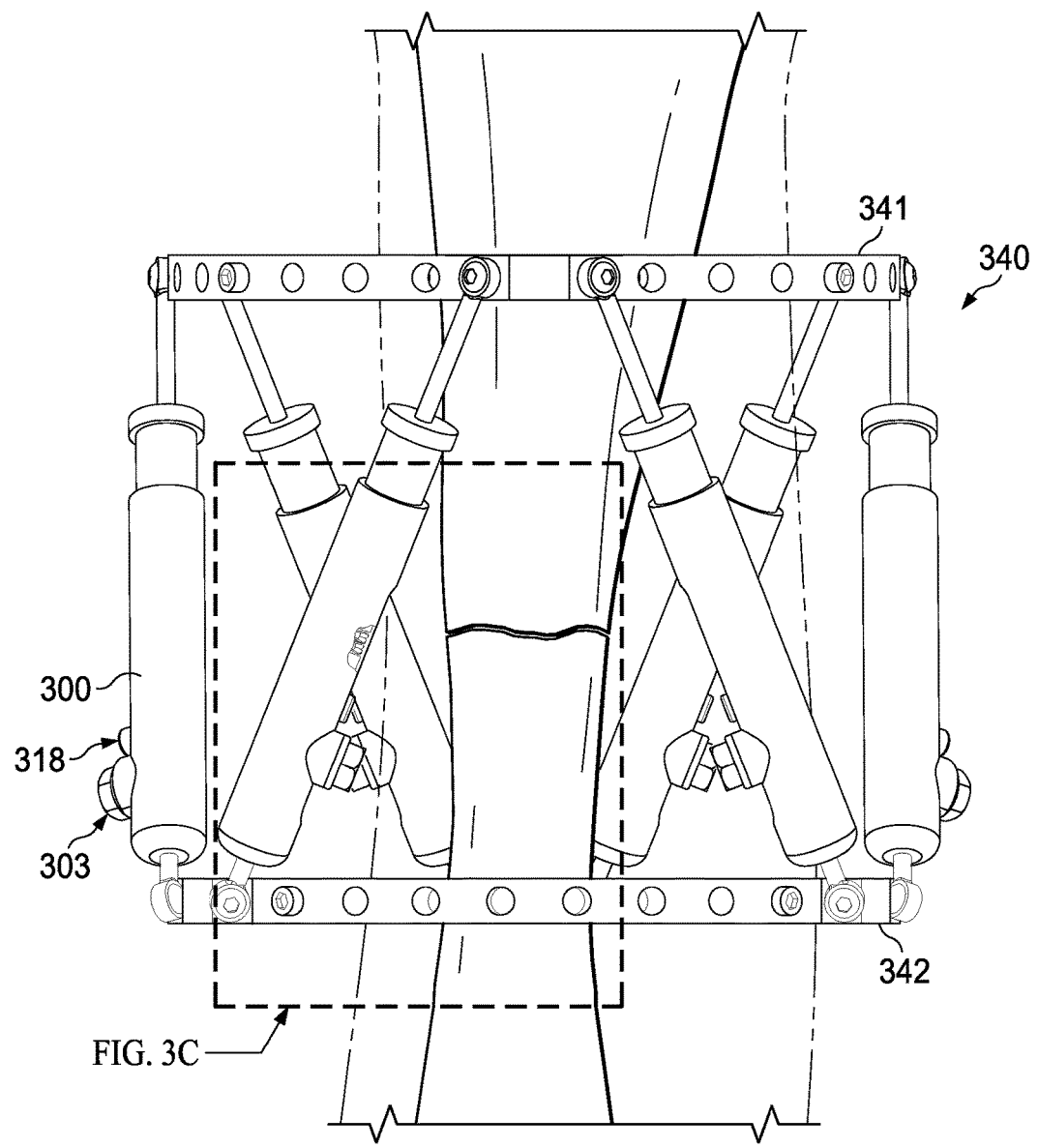
FIG. 3B is a view of an external fixation device surrounding a person's bone with a fracture.

FIGS. 3A-3F illustrate example embodiments of employing the external fixation device as described in the present application. FIG. 3A is a top view of a person's bone. In an embodiment, the bone may be a femur, tibia, or fibula. There are fractures on the person's bone. In an example embodiment, the facture may be a midshaft tibial fracture that requires treatment and healing. In other embodiments, the bone may belong to other parts of the person's body. FIG. 3B is a view of an embodiment of an external fixation device installed and surrounding the fractured bone. In an embodiment, the external fixation device is the same as the external fixation device 240 as shown in FIG. 2. The struts shown in FIG. 3B may be the same as the strut 100 as illustrated in FIGS. 1A-1H. Thus, like numerals will be employed for the external fixation device 340 in FIGS. 3B-3D. In an embodiment, the bone shown in FIGS. 3B-3D may be a femur, tibia, or fibula. In other embodiments, the bone may belong to other parts of the person's body. Since the bone shown in FIG. 3B can represent various bones of a person's body, in certain embodiments, the dimensions of the bone may be slightly out of proportion. In an embodiment, pins (not shown) attached to the external fixation device 340 are connected to the bones near a fracture that requires healing (e.g. person's tibia). The pins (not shown) may be drilled or pierced into the person's skin and bone for installation of the external fixation device 340. Connection of the external fixation device 340 to the bone(s) may include placing connectors, such as wires, pins, screws, and/or rods, among others through the skin and into, through, and/or around the selected bone(s).

Figure 3C:
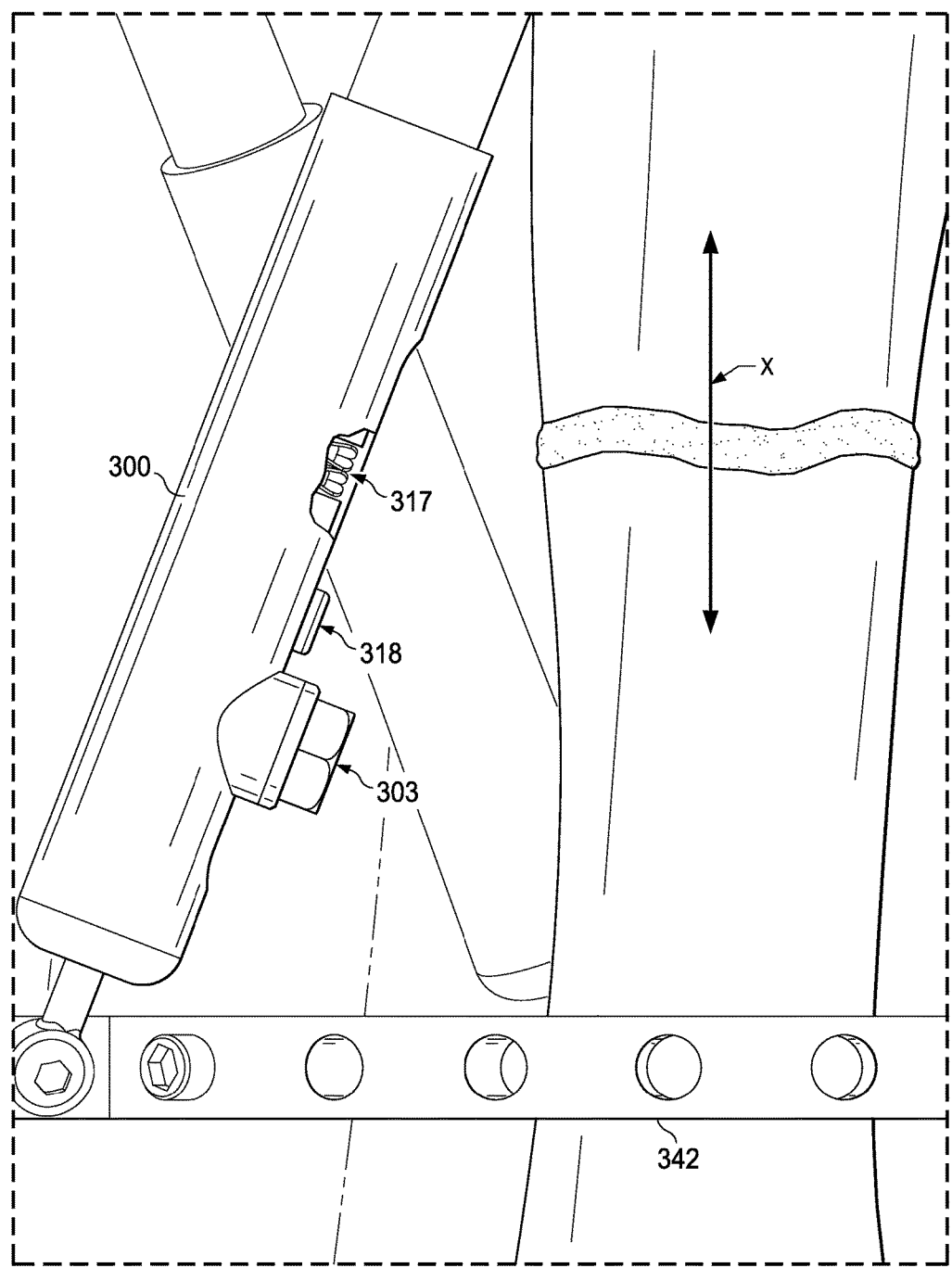
FIG. 3C is a close up view of FIG. 3B.
Figure 3D:
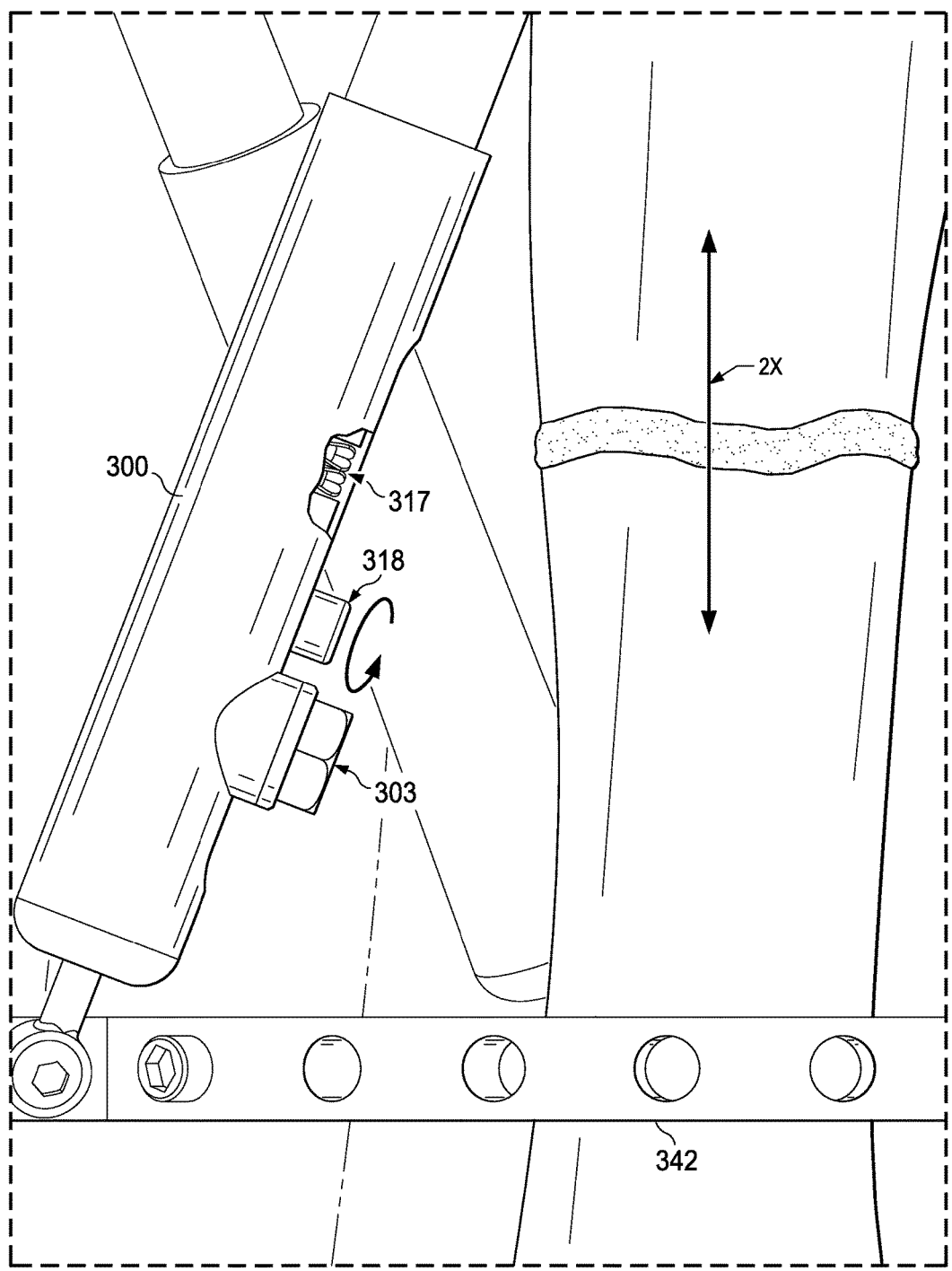
FIG. 3D is another close up view of FIG. 3B.
Figure 3E:
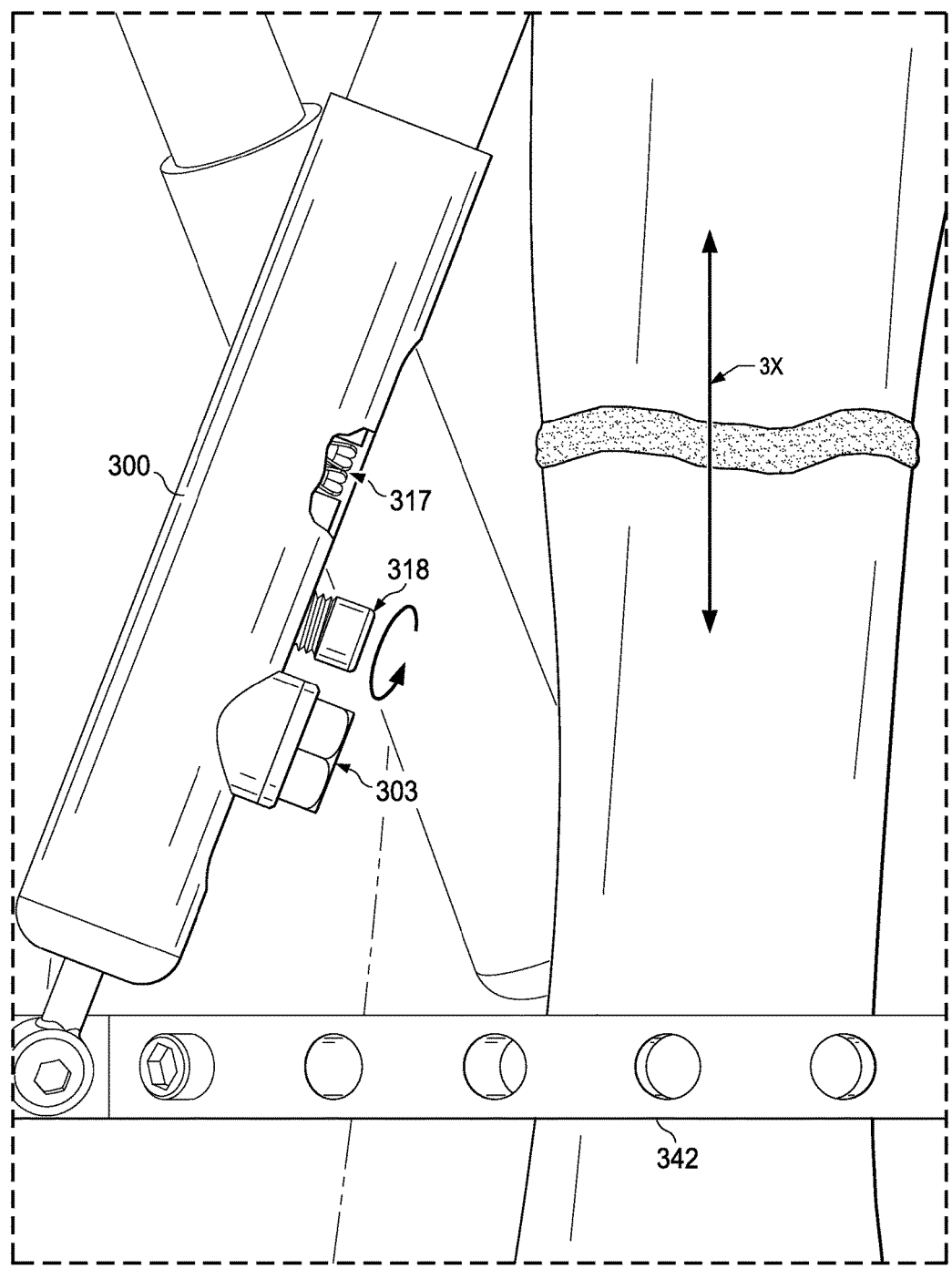
FIG. 3E is another close up view of FIG. 3B.

FIGS. 3C-3E are close up views of FIG. 3B, illustrating the dynamization process as described in the present application. In an embodiment, in FIG. 3C, the fracture is relatively new and the external fixation device 340 was installed relatively recently. In this embodiment, an element 318 of an adjustment mechanism 304 is tightened and a second sleeve member (not shown) is maximally displaced from a first sleeve member (not shown). A better view of the first sleeve member (not shown) and the second sleeve member (not shown) is shown in FIG. 1A. Thus, in this arrangement, relative movement between the first sleeve member and the second sleeve member is minimized, and a biasing mechanism 317 is minimally active. This provides less pressure on the fracture, thereby allowing it to heal. In an embodiment, the amount of pressure on the fracture is shown to be "x." In an embodiment, the pressure may be torsion, compression, and flexion.

In FIG. 3D, the fracture has healed more than the fracture shown in FIG. 3C. Here, a callous may have begun to form on the fractured bones, as illustrated by the fracture becoming more dense. As provided earlier in the present application, if the external fixation device 340 is too stable, at times, there may be certain disadvantages. These disadvantages may be addressed by destabilizing the external fixation device 340 in a controlled fashion. Thus, in an embodiment, the element 318 is loosened (e.g. unscrewed), thereby allowing relative movement between the first sleeve member (not shown) and the second sleeve member (not shown). This results in the biasing mechanism 317 becoming more active. This provides destabilization of the external fixation device 340, which exerts sufficient loading force and pressure to the patient's fractured body part (i.e., tibia) to accelerate the healing process. Here, the pressure may be "2X," which is double the amount of pressure exerted in FIG. 3C. But in other embodiments, the pressure may be any amount greater than "x." In an embodiment, the loading force and pressure may be torsion, compression, and flexion.

In FIG. 3E, the fracture has healed even more than the fracture shown in FIG. 3D. To provide further destabilization of the external fixation device 340, the element 318 is further loosened (e.g. unscrewed). Thus, the second sleeve member is minimally displaced from the first sleeve member. This allows relative movement between the first sleeve member and the second sleeve member, and the biasing mechanism 317 becomes more active than it is in FIGS. 3C and 3D. Hence, even more pressure (e.g. "3x") is exerted on the bone. But in other embodiments, the pressure may be any amount greater than "x." In an embodiment, the loading force and pressure may be torsion, compression, and flexion. Once again, such controlled destabilization of the external fixation device provides advantages such as accelerated healing.

Figure 3F:
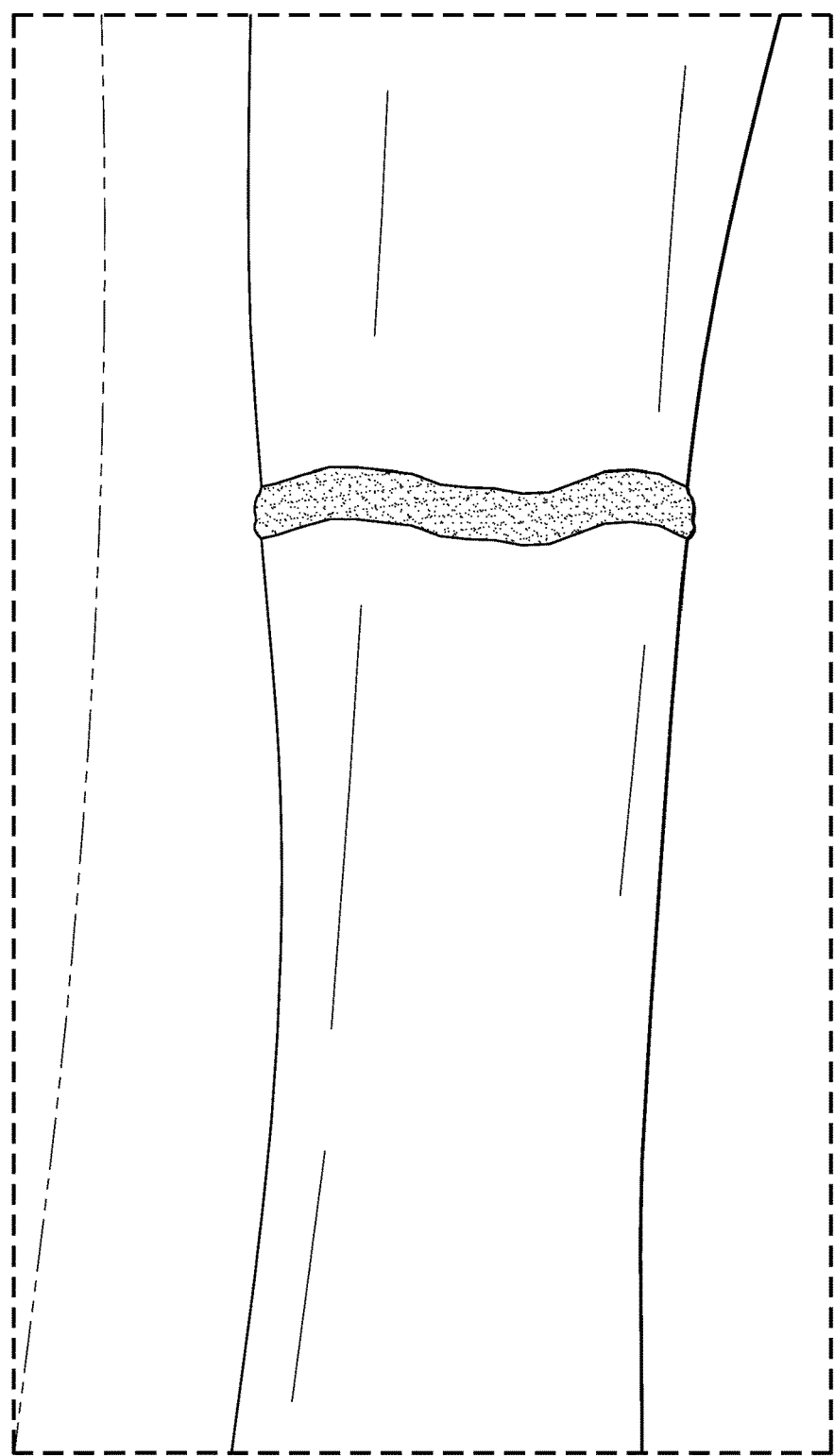
FIG. 3F is a view of a healed fracture.

FIG. 3F is a view of the bone after the healing process shown in FIGS. 3B-3E. Thus, FIGS. 3A-3F illustrate a loading process proceeding gradually during the mineralization phase of the fracture healing process. This will result in accelerated bone healing and in a stronger union of the fractured tissues.

It will be understood that particular embodiments described herein are shown by way of illustration and not as limitations of the disclosure. The principal features of this disclosure can be employed in various embodiments without departing from the scope of the disclosure. Those skilled in the art will recognize, or be able to ascertain using no more than routine experimentation, numerous equivalents to the specific procedures described herein. Such equivalents are considered to be within the scope of this disclosure and are covered by the claims.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A strut having a longitudinal axis defined therein, the strut comprising:
   a strut housing having at least a partial axial bore defined therethrough;
   an adjustment sleeve within the axial bore of the strut housing, the adjustment sleeve comprising:
      an adjustment bore extending from a top surface towards a bottom surface of the adjustment sleeve;
      a first sleeve member having a proximal end, a distal end, and at least a partial axial bore extending from the distal end towards the proximal end;
      a second sleeve member adjoining the first sleeve member, wherein the second sleeve member comprises a body having an outer surface that is substantially proximal to the distal end of the first sleeve member, the second sleeve member having a beveled end that is slidably disposed within the axial bore of the first sleeve member; and
      a biasing mechanism positioned between the first sleeve member and the second sleeve member;
   an adjustment mechanism that comprises an element that passes through the adjustment bore and comes in contact with the beveled end of the second sleeve member, wherein adjusting the element changes a vertical position of the element in relation to the adjustment sleeve and is thereby operable to control a longitudinal displacement of the beveled end that is in contact with the element and is slidably disposed within the axial bore of the first sleeve member.

2. The strut of claim 1, wherein the element may be in one of a first position or a second position, wherein
   in the first position, the element is tightened so that relative movement between the first sleeve member and the second sleeve member is minimized, and wherein
   in the second position, the element is loosened so that there is relative movement between the first sleeve member and the second sleeve member.

3. The strut of claim 2, wherein
   if the element is in the first position, the beveled end is in a distal position, and
   if the element is in the second position, the beveled end is in a proximal position, wherein
   the distal position is longitudinally placed further away than the proximal position from a proximal end of the axial bore of the first sleeve member.

4. The strut of claim 3, wherein
   if the beveled end is in the distal position, the biasing mechanism becomes less active, and
   if the beveled end is in the proximal position, the biasing mechanism becomes more active.

5. The strut of claim 4, wherein the element comprises a plurality of longitudinal grooves on an outer surface of the element, and wherein the adjustment mechanism further comprises a ball coupled with a second biasing member, wherein when the element is turned, the ball can releasably latch into one of the plurality of longitudinal grooves of the element.

6. The strut of claim 5, wherein the longitudinal placement of the beveled end of the second sleeve member can be quantifiably adjusted by turning the element from a first latched position to a second latched position.

7. The strut of claim 1, wherein the biasing mechanism between the first sleeve member and the second sleeve member is positioned between the distal end of the first sleeve member and the body of the second sleeve member.

8. The strut of claim 1, wherein the biasing mechanism is selected from at least one of a spring, coiled spring, tension/extension spring, compression spring, torsion spring, constant spring, variable spring, flat spring, machined spring, cantilever spring, helical spring, compression spring, volute spring, tension or extension spring, hairspring or balance spring, leaf spring, V-spring, belleville spring, a constant-force spring, gas spring, mainspring, progressive rate coil spring, spring washer, torsion spring, or a wave spring.

9. The strut of claim 1, wherein the biasing mechanism is any compressible component.

10. The strut of claim 1, wherein the outer surface of the second sleeve member is annular.

11. An adjustment sleeve that may be slidably disposed within an axial bore of a strut housing, the adjustment sleeve comprising:
   an adjustment bore extending from a top surface towards a bottom surface of the adjustment sleeve;
   a first sleeve member having a proximal end, a distal end, and at least a partial axial bore extending from the distal end towards the proximal end;
   a second sleeve member adjoining the first sleeve member, wherein the second sleeve member comprises a body having an outer surface that is substantially proximal to the distal end of the first sleeve member, the second sleeve member having a beveled end that is slidably disposed within the axial bore of the first sleeve member;

a biasing mechanism positioned between the first sleeve member and the second sleeve member; and an adjustment mechanism that comprises an element that passes through the adjustment bore and comes in contact with the beveled end of the second sleeve member, wherein adjusting the element changes a vertical position of the element in relation to the adjustment sleeve and is thereby operable to control a longitudinal displacement of the beveled end that is slidably disposed within the axial bore of the first sleeve member and is in contact with the element.

12. The adjustment sleeve of claim 11, wherein the element may be in one of a first position or a second position, wherein in the first position, the element is tightened so that relative movement between the first sleeve member and the second sleeve member is minimized, and wherein in the second position, the element is loosened so that there is relative movement between the first sleeve member and the second sleeve member.

13. The adjustment sleeve of claim 12, wherein if the element is in the first position, the beveled end is in a distal position, and if the element is in the second position, the beveled end is in a proximal position, wherein the distal position is longitudinally placed further away than the proximal position from a proximal end of the axial bore of the first sleeve member.

14. The adjustment sleeve of claim 13, wherein if the beveled end is in the distal position, the biasing mechanism becomes less active, and if the beveled end is in the proximal position, the biasing mechanism becomes more active.

15. The adjustment sleeve of claim 14, wherein the element comprises a plurality of longitudinal grooves on an outer surface of the element, and wherein the adjustment mechanism further comprises a ball coupled with a second biasing member, wherein when the element is turned, the ball can releasably latch into one of the plurality of longitudinal grooves of the element.

16. A strut having a longitudinal axis defined therein, the strut comprising:

a strut housing having a housing adjustment aperture and at least a partial axial bore defined therethrough;

an adjustment sleeve slidably disposed within the axial bore of the strut housing, the adjustment sleeve comprising:

first and second bores extending from a top surface towards a bottom surface of the adjustment sleeve;

a first sleeve member having a proximal end and a distal end, the distal end comprising a bevel;

a second sleeve member having a proximal end and a distal end, the second sleeve member adjoining the first sleeve member, wherein the second sleeve member comprises a body having an outer surface at the proximal end and comprises at least a partial axial bore extending from the proximal end towards the distal end that is slidably disposed around the beveled end of the first sleeve member; and a biasing mechanism positioned between the first sleeve member and the second sleeve member;

a fastener that releasably couples the strut housing to the adjustment sleeve, wherein the fastener extends from the housing adjustment aperture to the first bore; and an adjustment mechanism that comprises an element that passes through the second bore and comes in contact with the beveled end of the first sleeve member, wherein adjusting the element changes a vertical position of the element in relation to the adjustment sleeve and is thereby operable to control a longitudinal displacement of the beveled end that is in contact with the element so that the second sleeve member is slidably disposed around the beveled end of the first sleeve member.

17. The strut of claim 16, wherein the element may be in one of a first position or a second position, wherein in the first position, the element is tightened so that relative movement between the first sleeve member and the second sleeve member is minimized, and wherein in the second position, the element is loosened so that there is relative movement between the first sleeve member and the second sleeve member.

18. The strut of claim 17, wherein if the element is in the first position, the beveled end is in a proximal position, and if the element is in the second position, the beveled end is in a distal position, wherein the distal position is longitudinally placed closer than the proximal position from a proximal end of the axial bore of the second sleeve member.

19. The strut of claim 18, wherein if the beveled end is in the proximal position, the biasing mechanism becomes less active, and if the beveled end is in the distal position, the biasing mechanism becomes more active.

20. The strut of claim 19, wherein the element comprises a plurality of longitudinal grooves on an outer surface of the element, and wherein the adjustment mechanism further comprises a ball coupled with a second biasing member, wherein when the element is turned, the ball can releasably latch into one of the plurality of longitudinal grooves of the element.

21. The strut of claim 16, wherein the biasing mechanism is any compressible component.

22. The strut of claim 16, wherein the outer surface of the second sleeve member is annular.

23. An adjustment sleeve that may be slidably disposed within an axial bore of a strut housing, the adjustment sleeve comprising:

first and second bores extending from a top surface towards a bottom surface of the adjustment sleeve;

a first sleeve member having a proximal end and a distal end, the distal end comprising a bevel;

a second sleeve member having a proximal end and a distal end, the second sleeve member adjoining the first sleeve member, wherein the second sleeve member comprises a body having an outer surface at the proximal end and comprises at least a partial axial bore extending from the proximal end towards the distal end that is slidably disposed around the beveled end of the first sleeve member; and a biasing mechanism positioned between the first sleeve member and the second sleeve member; and an adjustment mechanism that comprises an element that passes through the second bore and comes in contact with the beveled end of the first sleeve member, wherein adjusting the element changes a vertical position of the element in relation to the adjustment sleeve and is thereby operable to control a longitudinal displacement of the beveled end that is in contact with the element so that the second sleeve member is slidably disposed around the beveled end of the first sleeve member.

24. The adjustment sleeve of claim 23, wherein the element may be in one of a first position or a second position, wherein
in the first position, the element is tightened so that relative movement between the first sleeve member and the second sleeve member is minimized, and wherein
in the second position, the element is loosened so that there is relative movement between the first sleeve member and the second sleeve member.

25. The adjustment sleeve of claim 24, wherein
if the element is in the first position, the beveled end is in a proximal position, and
if the element is in the second position, the beveled end is in a distal position, wherein the distal position is longitudinally placed closer than the proximal position from a proximal end of the axial bore of the second sleeve member.

26. The adjustment sleeve of claim 25, wherein
if the beveled end is in the proximal position, the biasing mechanism becomes less active, and
if the beveled end is in the distal position, the biasing mechanism becomes more active.

27. The adjustment sleeve of claim 26, wherein the element comprises a plurality of longitudinal grooves on an outer surface of the element, and wherein the adjustment mechanism further comprises a ball coupled with a second biasing member, wherein when the element is turned, the ball can releasably latch into one of the plurality of longitudinal grooves of the element.

* * * * *